United States Patent [19]

Heath et al.

[11] Patent Number: 4,565,696

[45] Date of Patent: Jan. 21, 1986

[54] PRODUCTION OF IMMUNOGENS BY ANTIGEN CONJUGATION TO LIPOSOMES

[75] Inventors: Timothy D. Heath, San Francisco, Calif.; Pang Shek, Willowdale, Canada; Demetrios Papahadjopoulos, San Francisco, Calif.

[73] Assignee: The Regents of the University of California, Berkeley, Calif.

[21] Appl. No.: 520,090

[22] Filed: Aug. 3, 1983

[51] Int. Cl.[4] ................. A61K 39/00; A61K 31/00; A61K 9/22; A61K 9/52; A61K 31/682; A61K 47/00; C07G 7/00; G01N 33/54

[52] U.S. Cl. ............................. 424/88; 424/19; 424/78; 424/785; 514/2; 514/6; 260/112B; 260/112 R; 435/7; 435/177; 435/181; 436/822; 436/823

[58] Field of Search ............... 424/19, 85, 199, 88, 424/365, 177; 260/112 R, 112 B; 435/7, 177, 181; 436/822, 823

[56] References Cited

FOREIGN PATENT DOCUMENTS 0036277  9/1981  European Pat. Off. ............... 435/7

OTHER PUBLICATIONS

Martin, Francis J. et al., *J. Biol. Chem.* (1982), v. 257, p. 286, "Irreversible Coupling of IgG Fragments to Preformed Vesicles".

Shek, Pang et al., *Immunology,* v. 45, p. 349 (1981), "Immune Response Mediated by Liposome-Associated Protein Antigens".

Carlsson, Jan et al., *Biochem. J.* (1978), v. 173, pp. 723–737, "Protein Thiolation and Reversible Protein--Protein Conjugation".

McCormick, Patrick, *Chem. Abstracts,* v. 94, 61129m, "Coupling of BSA to Liposomes . . . ".

Freise, J. et al., *Chem Abstracts,* v. 94, 180599z.

Romanycheva et al., *Chem Abstr.,* v. 84, No. 99405c, 1976, "Kinetics of Immunodepressive Action of Methotretate".

McCormick, Patrick Joseph, *Diss. Abstr.,* No. 2064b, 1980, v. 41(b), p. 2064, "The Coupling of BSA to Liposomer Via Tolylene-2,4–Diisocyanate".

*Primary Examiner*—Thomas G. Wiseman
*Assistant Examiner*—Robin Lyn Teskin
*Attorney, Agent, or Firm*—Bertram I. Rowland

[57] ABSTRACT

Enhanced immunogenicity is achieved by covalently linking immunogens to liposomes and injecting the membrane-bound-proteins into an appropriate vertebrate host. Methods and compositions are provided for producing antibodies.

3 Claims, No Drawings

PRODUCTION OF IMMUNOGENS BY ANTIGEN CONJUGATION TO LIPOSOMES

This invention was made with Government support under Grant No. CA 25526-03 awarded by the Department of Health and Human Services. The Government has certain rights in this invention.

BACKGROUND OF THE INVENTION

1. Field of the Invention

There is an increasing interest in improving and varying the capability of preparing antibodies to a wide variety of determinant sites. The use of antibodies has been greatly expanded in diagnostics and therapy. The unique capability of antibodies to bind to a specific determinant site or chemical structure makes them peculiarly useful in directing drugs, radioisotopes, or markers to a particular site in a host. In addition, the ability of antibodies to distinguish a specific structure from similar structures has resulted in their wide use in diagnosis.

Regardless of whether one wishes monoclonal or polyclonal antibodies, the initial step is the immunization of a host. Usually, one hyperimmunizes the host by repeated injections of the immunogen in accordance with a predetermined schedule. Adjuvants are added to potentiate the immune response. Various adjuvants include aluminum and calcium salts, emulsifying adjuvants and bacteria, e.g. mycobacteria and corynebacteria.

In the case of monoclonal antibodies it is particularly desirable to enhance the immune response to specific epitopic sites. Since the preparation of monoclonal antibodies requires the detection of low population events, any technique which enhances the B-lymphocyte population of interest can prove to be important in the production of monoclonal antibodies.

2. Description of the Prior Art

Allison and Gregoriadis, *Nature (London)* (1974) 252:252; Heath et al., *Biochem. Soc. Trans.* (1976) 4:129; and Shek and Sabiston, *Immunology* (1982) 45:349 describe potentiating the immune response by incorporating antigens in liposomes. Shek and Sabiston, *Immunology* (1982) 47:627; Shek, (1983) Applications of liposomes in immunopotentiation. In: Immunotoxicology, NATO Advanced Study Institute Series (P. W. Mullen, ed.) Springer-Verlag, Heidelberg; and Van Rooijen and Van Nieuwmegen, *Immunol. Commun.* (1980) 9:243 describe the use of liposomes with immunogens bound to the membrane surface. Leserman et al., *Nature* (1980) 228:602; Heath et al., *Biochem. Biophys. Acta.* (1980) 599:42; Heath et al., ibid. (1981) 640:66 and Martin and Papahadjopoulos, *J. Biol. Chem.* (1982) 257:286 describe the covalent bonding of proteins to lipid vesicles, which disclosure is incorporated herein by reference. See also U.S. Pat. Nos. 4,235,871 and 4,241,046, particularly columns 3-5 of U.S. Pat. No. 4,235,871, which subject matter is incorporated herein by reference.

SUMMARY OF THE INVENTION

Methods and compositions are provided for potentiating the immune response, whereby immunogens are covalently linked to vesicle surfaces. A minimum ratio of immunogen to lipid is provided for optimizing immune response.

DESCRIPTION OF THE SPECIFIC EMBODIMENTS

In accordance with the subject invention, methods and compositions are provided for producing antibodies to antigenic materials. The compositions involved are liposomes to which the antigens are covalently bonded to the surface above a minimum ratio of protein to lipid. The proteins may be bonded to one or more lipid molecules which are involved in the vesicle membrane.

The compositions of the subject invention can be conveniently prepared by preparing liposomes having active functionalities which can be used for linking by means of a convenient linking group to the antigen. The liposomes may be prepared from a wide variety of lipid materials including phosphatidyl ethers and esters, e.g. phosphatidylethanolamine, phosphatidylcholine, etc.; glycerides, cerebrosides, gangliosides, sphingomyelin, steroids, e.g. cholesterol; etc. See U.S. Pat. No. 4,235,871 for additional lipid materials for use in the preparation of liposomes. One or more of the lipid molecules will be present in minor amount, generally ranging from about 1 to 15 mole percent, more usually ranging from about 2 to 12 mole percent, which will have an active functionality which may be used for linking. Functionalities which may be present include activated olefins, particularly olefins having from 1 to 2 carbonyl groups bonded to the olefin, e.g. acrylates and maleimide, aldehydes, carboxylic acids, or the like. Preferably, the active functionality will be an activated olefin.

The antigen will for the most part be a poly(amino acid), including peptides and proteins, which may also include prosthetic groups. The antigen may or may not require modification in order to be linked to the active functionality of a liposome. For linking the activated olefin, thiol functionalities are particularly useful. The resulting thioether is a stable link which provides for the stable retention of the antigen to the vesicle surface. Where the antigen does not naturally have available thiol groups, these can be introduced in a variety of ways with a variety of conventional reagents, such as 3-(2'-pyridylthio)propionate, methyldithioacetic acid, dinitrophenylthioacetic acid, or the like. There will be at least one thio functionality per antigen molecule, preferably at least two thio functionalities and usually not more than one thio functionality per 2000 daltons, more usually not more than one thio functionality per 3000 daltons. Martin and Papahadjopoulos, supra, disclose an exemplary method for bonding proteins to liposomes employing a thioether link.

The aldehyde and carboxy functionalities can be linked to available amino groups of the antigen, in the former case with reductive amination and in the latter case by employing carbodiimide or esters capable of forming peptide bonds in an aqueous medium.

The vesicles may be prepared in conventional ways by combining the lipids in appropriate ratios and vigorously agitating the mixture so as to produce the vesicles. Vesicle preparation may be achieved by the following techniques: See, for example, Leserman et al., *Nature* (1980) 228:602; Heath et al., *Biochem. Biophys. Acta.* (1981) 640:66; and Martin and Papahadjopoulos, *J. Biol. Chem.* (1982) 257:286, whose relevant disclosure is incorporated herein by reference.

The antigen or modified antigen may be joined to a dispersion of the vesicles in an appropriate ratio under conditions where covalent bonds are formed between the vesicle and the antigen. Desirably, there should be at least about 25 g of protein per mole of lipid, more preferably at least about 40 g of protein per mole of lipid and preferably at least about 50 g of protein per mole of lipid. There is generally no need to saturate the surface with protein to achieve the desired degree of immunogenicity, so that in most cases, the amount of protein bound to the surface will be less than saturation.

Once the vesicle-protein conjugate has been prepared, it may be purified in accordance with conventional techniques. Conveniently, the conjugated liposomes may be separated from unbound protein by flotation on an appropriate liquid gradient.

Of particular interest is the presence of immunomodulators enclosed in the aqueous space or in the bilayer of the vesicle-antigen conjugate. The immunomodulators can serve to modulate the immune response by interacting preferentially or exclusively with certain subpopulations of cells, e.g. suppressor or helper T-cells, B-cells, macrophages, or the like. For the most part, immunomodulators will be compounds having a specific interaction or affinity for a particular subpopulation of cells which may be recognized by one or more unique determinant sites.

The types of compounds which find use as immunomodulators may be very diverse. The compounds may be immunostimulators, such as hydrophobic or hydrophilic derivatives of muramyldipeptide, a derivative of bacterial cell walls, which acts as an immunostimulator and a potentiator of macrophage tumoricidal effects. Other bacterial isolates known to affect lymphocytes or macrophages may also find use.

Various drugs which act as immunopotentiators may be employed, such as levamisole, niridazole, oxysuran or flagyl.

Another group of compounds which could find use are cytotoxic agents or cell growth inhibitors, particularly where the liposome is specifically directed to interact with particular lymphocyte subpopulations, e.g. by the use of antibodies or other specific receptor molecules. Such compounds may include enzyme inhibitors, such as methotrexate and its derivatives; corticosteroids; alkylating agents, such as chlorambucil, melphalan and the nitrosoureas; anthracyclines, such as adriamycin; vinca alkaloids, such as vincristine; antitumor antibiotics, such as deoxycoformycin, actinomycin D, mitomycin, bleomycin, cisplatin, cytochalasin B, colchicine, etc; the A chain of toxins, e.g. ricin and diphtheria; or the like.

The concentrations of the various immunomodulators will vary widely depending on the particular immunomodulator, its intended function, the host, the concentration of vesicles administered to the host, the solubility of the compound, and the like. Therefore, for the most part, the concentration employed will be determined empirically.

It is believed that T-suppressor cells will bind to the liposomes of the present invention. To that extent the proliferation of the T-suppressor cells which bind to the antigen—antigenic or epitopic site—conjugated to the vesicle can be modulated. By suppressing the proliferation of such cells, antibody production may be enhanced. Of particular interest are compounds which inhibit proliferation, such as enzyme inhibitors, e.g. methotrexate, antitumor antibiotics, or the like.

The vesicle-antigen conjugate may be administered through a vertebrate host in accordance with conventional ways. The vesicle-antigen conjugates may be administered intraperitoneally, subcutaneously, intravenously or intramuscularly. The administered dose will vary depending upon the antigen and the host. Usually, total dosages administered at a single time will be less than about 0.5 mg/kg of host, usually less than about 0.25 mg/kg of host, and at least about 25 $\mu$g/kg of host, more usually at least about 50 $\mu$g/kg of host.

The vesicle-protein conjugates may be used for the production of monoclonal or polyclonal antibodies. In some instances, the vesicle-protein conjugates may be combined with peripheral blood cells, transformed B-lymphocytes, or the like to provide for the production of antibodies.

EXPERIMENTAL

Materials and Methods

Animals

Male A/J mice, 6 to 8 weeks old, were purchased from the Jackson Laboratories, Bar Harbor, Me. Animals were kept in plastic cages and were allowed free access to laboratory mouse chow and water.

Chemicals and Biologicals

Citrated sheep's blood was supplied by Woodlyn Laboratories, Guelph, Ontario. Phosphatidylcholine and cholesterol were purified as described by Heath et al., *Biochem. Biophys. Acta.* (1981) 640:66. N-[4-(p-maleimidophenyl)butyryl]phosphatidylethanolamine (MPB-PE) was synthesized as described in Martin and Papahadjopoulos, *J. Biol. Chem.* (1982) 257:286.

Preparation of Reverse-Phase Evaporation Vesicles (REV)

Liposomes were prepared from phosphatidylcholine:cholesterol:MPB-PE at a molar ratio of 47:47:6 by the method of Szoka and Papahadjopoulos, *Proc. Natl. Acad. Sci. USA* (1978) 75:4194. The buffer was 50 mM morpholinoethanesulphonic acid (MES), 50 mM morpholinopropanesulphonic acid (MOPS), 80 mM NaCl (MES/MOPS), pH 6.7, 290 mOsm.

Covalent Conjugation of BSA to Vesicle Surface

Bovine serum albumin (BSA) was dissolved in 0.1 M phosphate, 0.1 M NaCl, pH 7.5 at 20 mg/ml. SPDP (N-succinimidyl 3-(2'-pyridylthio)propionate) was prepared at 20 mM in ethanol. Sufficient SPDP solution was added to the BSA solution with stirring, to give a 20:1 molar ratio of SPDP:protein. After 30 min the 3-(2'-pyridylthio)propionate-BSA (PDP-BSA) was separated from reactants by gel chromatography on a Sephadex G-75 column prepared in 50 mM citrate, 50 mM phosphate, 50 mM NaCl, pH 7.0. The PDP:protein ratio was determined by the method of Carlson et al. *Biochem. J.* (1978) 173:723 and found to be 13.5 PDP groups per BSA molecule. Preliminary experiments showed that this number of thiols was necessary to achieve efficient conjugation. The PDP-BSA solution was adjusted to pH 4.5 and treated with dithiothreitol to a final concentration of 25 mM. After 30 min, the reduced protein was separated from dithiothreitol by gel chromatography on Sephadex G-75. The column was equilibrated with MES/MOPS (pH 6.7, 290 mOsm) and purged with argon. The thiol-BSA peak was collected under argon and concentrated to 12 mg/ml in a 10 ml Amicon concentrator cell with YM-10 membrane.

Conjugation was initiated by mixing liposomes with thiol-BSA at various concentrations to control the final product. (See Table 1) After overnight conjugation, the liposomes were separated from unbound protein by flotation on a discontinuous metrizamide gradient (Heath et al. (1981), supra.). The liposomes were analyzed for protein and lipid content as described in the immediately preceding reference.

Preparation of Methotrexate Encaptured BSA-vesicle Conjugates

Liposomes were prepared from phosphatidylcholine:cholesterol:MPB-PE at a molar ratio of 47:47:6 by the method of Szoka and Papahadjopoulos, supra. The liposomes were prepared in a solution which contained 50 mM methotrexate (sodium salt), 50 mM morpholinoethanesulphonic acid, 50 mM morpholinopropanesulphonic acid, pH 6.7, 290 mOsm. When the liposomes are prepared, a proportion of the solution, the methotrexate, is captured in the aqueous interstices of the liposomes. The non-encapsulated material is separated chromatographically from the liposomes on a column of Sephadex G75 which is equilibrated with a buffer composed of 50 mM morpholinoethanesulfonic acid, 50 mM morpholinopropanesulfonic acid, 80 mM NaCl, pH 6.7, 290 mOsm. The liposomes are then conjugated to the bovine serum albumin as described below.

When the final product is isolated from the gradient, it is analysed for protein, lipid and drug content. The drug is measured spectrophotometrically ($\epsilon_{cm} = 7943$ at 370 nm) after extraction by the Bligh and Dyer method, which separates the drug from the lipid, thereby giving an optically clear suspension.

Haemolytic Plaque Assay

The procedures used for the preparation of spleen cells and for the determination of the BSA-specific plaque-forming cell (PFC) response were performed as described by Shek and Sabiston, *Immunology* (1982) 45:349.

TABLE 1

Effect of the initial protein concentration on protein:lipid conjugate ratio in the coupling of BSA to liposomes*

| Experiment Number | Starting Reaction | | Product |
|---|---|---|---|
| | Protein Conc. (mg/ml) | Lipid Conc. (μmole/ml) | Protein:Lipid (μg/μmole) |
| 1 | 8.80 | 6.9 | 174 |
| 1 | 4.45 | 6.9 | 156 |
| 1 | 2.18 | 6.9 | 130 |
| 1 | 0.53 | 6.9 | 36 |
| 2 | 13.64 | 6.0 | 245 |
| 2 | 2.0 | 6.0 | 135 |
| 2 | 1.0 | 6.0 | 57 |
| 2 | 0.5 | 6.0 | 41 |
| 2 | 0.25 | 6.0 | 24 |

*Liposomes were prepared, conjugated, separated and analysed as described in Materials and Methods.

Results

As evidenced by the results reported in Table 1, variation of the initial protein concentration of the reaction mixture between 0.25 and 2 mg/cl caused large variations in the lipid:protein ratio of the product. However, when the initial protein concentration was increased above 2 mg/ml, the final protein:lipid ratio of the product rose less rapidly. This would indicate that at approximately 130 μg/μmole, the BSA may saturate the outer liposome surface, thereby inhibiting further significant attachment.

PFC Response to BSA Antigen Conjugated to Liposome Surface

Mice were given two intraperitoneal injections, 3 weeks apart, of BSA-conjugated vesicles containing 30 μg of BSA. The BSA-specific PFC response was assayed 3 to 5 days after the second injection of antigen.

The peak anti-BSA PFC response occurred on Day 4. At the peak of the response, essentially the same number of PFC was generated whether the immunizing dose contains 7 or 30 μg of BSA. (See Table 2.)

Different control groups of animals injected with native BSA, thiolated BSA, or unconjugated vesicles failed to elicit a detectable PFC response. The simultaneous injection of liposomes and thiolated BSA was also found to be ineffective in engendering a significant response.

Liposomal vesicles coated with BSA at different protein:lipid ratio (epitope density) were tested for their effectiveness in stimulating the PFC response to the protein antigen. At an immunizing dose of 30 μg, there was no difference in the PFC elicited with antigen-coated vesicles containing approximately 60 to 250 μg BSA/μmole lipid. However, the magnitude of the response decreased significantly at an epitope density of 40 μg BSA/μmole lipid or less.

TABLE 2

Immunogenicity of different preparations of BSA, conjugated and unconjugated liposomal vesicles in A/J mice

| Groups[a] | Antigens | Immunizing Dose[c] | | BSA-specific IgG PFC/10[6] spleen cells[d] ± S.E.M. |
|---|---|---|---|---|
| | | BSA (μg) | Lipid (μmole) | |
| (A) | BSA-conjugated vesicles[b] | 30 | 0.17 | 395 ± 54 |
| (B) | BSA-conjugated vesicles | 7 | 0.04 | 390 ± 52 |
| (C) | Unconjugated vesicles | — | 0.20 | <10 |
| (D) | Thiolated BSA | 30 | — | <10 |
| (E) | Unconjugated vesicles + Thiolated BSA | 30 | 0.20 | <10 |
| (F) | Native BSA | 30 | — | <10 |

[a]4 animals in each group.
[b]BSA was conjugated to the vesicle surface at a ratio of 174 μg protein/μmole lipid.
[c]Animals were given two intraperitoneal injections of the same dose of antigen, three weeks apart.
[d]The BSA-specific PFC response was assayed four days after antigenic challenge.

In the next study, mice were immunized twice with BSA attached to liposomes. Group A received 2×20 μg BSA conjugated with liposomes (ratio 6 g/mol). Group B received liposome BSA as in Group A, but with 0.05 μmole of methotrexate. Group C received 0.05 μmole of methotrexate in liposomes conjugated with 20 μg BSA. Group D received 20 μg BSA conjugated to liposomes and 0.05 μmole methotrexate in a separate population of liposomes. The results were determined as BSA-specific plaque-forming cell (PFC) response. The following are the results.

| Group | BSA-specific IgG PFC/10[6] spleen cells* |
|---|---|
| A | 300 |
| B | 350 |
| C | 950 |
| D | 50 |

*Assayed four days after antigenic challenge.

The extraordinary enhancement in response with the methotrexate in the vesicle conjugated with BSA is evident.

It is evident from the above results that by covalently conjugating protein to liposomes above a minimum epitopic density, enhanced immunogenic responses can be achieved. Furthermore, the liposomes can serve as vessels for various substances which may serve to further enhance the immune response. In accordance with this invention, a simple effective procedure and compositions are provided for eliciting antibodies to one or more epitopes of an antigenic material.

Although the foregoing invention has been described in some detail by way of illustration and example for purposes of clarity of understanding, it will be obvious that certain changes and modifications may be practiced within the scope of the appended claims.

What is claimed is:

1. In a method for eliciting an immune response for the production of antibodies to a predetermined antigen, wherein an immunogen containing said predetermined antigen is administered to a vertebrate host resulting in the production of antibodies, the improvement which comprises employing as the immunogen, antigen covalently bound to the membrane of a liposome, said antigen being present in at least about 25 grams of antigen per mole of lipid, where said liposome internally contains an antibody enhancing effective amount of a cell growth inhibitor.

2. A method according to claim 1, wherein said cell growth inhibitor is an enzyme inhibitor.

3. A method according to claim 2, wherein said enzyme inhibitor is methotrexate.

* * * * *